United States Patent [19]
Shulze

[11] Patent Number: 6,117,086
[45] Date of Patent: Sep. 12, 2000

[54] PRESSURE TRANSDUCER APPARATUS WITH DISPOSABLE DOME

[75] Inventor: John E. Shulze, Rancho Santa Margarita, Calif.

[73] Assignee: Sunscope International, Inc., Newport Beach, Calif.

[21] Appl. No.: 08/844,236

[22] Filed: Apr. 18, 1997

Related U.S. Application Data

[63] Continuation-in-part of application No. 08/635,432, Apr. 19, 1996.

[51] Int. Cl.[7] ........................................ A61B 5/00
[52] U.S. Cl. .......................... 600/488; 600/486; 600/561; 73/706; 73/721
[58] Field of Search ................................... 600/485–488, 600/561; 73/715, 721, 726–727

[56] References Cited

U.S. PATENT DOCUMENTS

| | | |
|---|---|---|
| 3,818,765 | 6/1974 | Eriksen . |
| 4,023,562 | 5/1977 | Hynecek et al. . |
| 4,072,056 | 2/1978 | Lee . |
| 4,160,575 | 7/1979 | Schraut . |
| 4,230,391 | 10/1980 | Keglewitsch . |
| 4,314,480 | 2/1982 | Becker . |
| 4,317,126 | 2/1982 | Gragg, Jr. . |
| 4,398,542 | 8/1983 | Cunningham et al. . |
| 4,407,296 | 10/1983 | Anderson . |
| 4,465,075 | 8/1984 | Swartz . |
| 4,505,157 | 3/1985 | Le . |
| 4,529,789 | 7/1985 | Kroupa . |
| 4,554,927 | 11/1985 | Fussell . |
| 4,557,269 | 12/1985 | Reynolds et al. . |
| 4,576,181 | 3/1986 | Wallace et al. . |
| 4,589,287 | 5/1986 | Dickens . |
| 4,610,256 | 9/1986 | Wallace . |
| 4,644,797 | 2/1987 | Ichikawa et al. . |
| 4,679,567 | 7/1987 | Hanlon et al. . |

(List continued on next page.)

FOREIGN PATENT DOCUMENTS

| | | |
|---|---|---|
| 2005297 | 6/1990 | Canada . |
| WO8602446 | 4/1986 | WIPO . |
| WO9006722 | 6/1990 | WIPO . |
| WO9701363 | 1/1997 | WIPO . |
| WO9701364 | 1/1997 | WIPO . |

OTHER PUBLICATIONS

Safeset™ Arterial Pressure Tubing, Abbott Critical Care Systems Brochure 1993.
Vamp™ Jr. Venous/Arterial Blood Management Protection System for neonatal and pediatric applications. Baxter Brochure.
Vamp™, Venous/Arterial Blood Management Protection System. Baxter Brochure.
Argon CDXpress® Disposable Pressure Transducer. Maxxim Medical Brochure.
Deltran™, Technology for Critical Care. Utah Medical Products, Inc. Brochure.

*Primary Examiner*—Cary O'Connor
*Assistant Examiner*—Ryan Castes
*Attorney, Agent, or Firm*—Stout, Uxa, Bryan & Mullins LLP; Donald E. Stout

[57] ABSTRACT

A physiological pressure transducer is disclosed which can be adapted for multiple uses and which employs a low cost semiconductor strain gauge sensor. The transducer is connected to a fluid-filled catheter/manometer system for measuring pressures inside a living body in areas of medical interest such as the heart, brain, uterus, or the vascular system. The catheter is coupled to the pressure transducer through a unique, disposable dome containing a shaped, compliant isolation media which is in intimate contact with the transducer diaphragm. The complete assembly is adapted for use with standard catheter flushing solutions and flush devices. An improved method of drawing blood samples by using the features of the assembly is also described.

15 Claims, 13 Drawing Sheets

U.S. PATENT DOCUMENTS

| | | |
|---|---|---|
| 4,683,894 | 8/1987 | Kodama et al. . |
| 4,686,764 | 8/1987 | Adams et al. . |
| 4,776,343 | 10/1988 | Hubbard et al. . |
| 4,825,876 | 5/1989 | Beard . |
| 4,885,983 | 12/1989 | Zavoda . |
| 4,920,972 | 5/1990 | Frank et al. . |
| 5,042,495 | 8/1991 | Spotts et al. . |
| 5,097,841 | 3/1992 | Moriuchi et al. . |
| 5,417,395 | 5/1995 | Fowler et al. . |
| 5,429,804 | 7/1995 | Sayles . |
| 5,461,922 | 10/1995 | Koen . |
| 5,522,266 | 6/1996 | Nicholson et al. . |
| 5,551,300 | 9/1996 | Vurek et al. . |
| 5,752,918 | 5/1998 | Fowler et al. ................... 600/488 |

PRESSURE TRANSDUCER APPARATUS WITH DISPOSABLE DOME

This is a continuation-in-part of my copending application Ser. No. 08/635,432, titled Pressure Transducer Apparatus and Disposable Dome, and filed Apr. 19, 1996.

BACKGROUND OF THE INVENTION

The present invention relates to medical fluid pressure transducers, and, more particularly, to fluid pressure transducers for invasive blood pressure measurements having a reusable component and a one time use disposable component.

Since the 1970s, physiological blood pressure monitoring became widely employed for diagnosis and treatment of patients experiencing hemodynamic instability during surgery and in other forms of acute illness. An arterial cannula, central venous catheter, or pulmonary artery catheter is inserted into a blood vessel using a Seldinger percutaneous puncture technique, the puncture wound is dilated, then the catheter is inserted into the vessel, the catheter is attached to a saline-filled pressure monitoring line, blood pressure transducer, pressurized fluid supply, and sterile fluid flushing device, and finally the transducer's electrical interface cable is attached to an electronic blood pressure amplifier and display monitor. Once calibrated, such systems give accurate and up to date readouts of the constantly changing blood pressure levels at the tip of the catheter within the cardiovascular system.

Similarly, catheters and techniques have been developed for direct insertion of fluid filled catheters into the brain for the monitoring of increased intra-cranial pressures resulting from acute brain injury, and for insertion into the uterus during childbirth to monitor the strength and character of contractions through changes in the amniotic fluid pressure. Many of these same prior-art transducer systems have been and continue to be employed for this entire range of measuring applications, plus other physiological monitoring or biological fluid pressure measurement applications within living bodies.

A typical early prior art device includes a removable (single use disposable) dome with an inlet and an outlet port for flushing and filling of the transducer assembly with sterile isotonic saline solution. The dome is made of a clear molded plastic material such as polycarbonate so that air bubbles in the flushing fluid could be observed and removed. A flushing device, such as ones described in U.S. Pat. Nos. 4,291,702 to Cole or 3,675,891 to Reynolds is typically affixed to the dome's side port for the purpose of providing a continuous flow of saline through the dome and into the catheter. A "fast flush" valve on the flush device may be activated to temporarily select a higher flow rate for filling, de-bubbling, or clearing of blood in the dome and/or catheter.

The early prior art blood pressure transducers were made with a metal diaphragm forming a pressure sensitive area on an external surface of the transducer housing. The diaphragm was coupled internally to a mechanical push rod linkage assembly and a strain-sensing device, such as an unbonded wire strain gauge constructed in a Wheatstone Bridge configuration. The pressure sensitive area of the metal diaphragm is now typically isolated from the sterile saline being flushed into the catheter by a thin polycarbonate or nitrile rubber diaphragm on the mating surface of a single use dome. Such disposable domes are typically supplied sterile and discarded after a single use to avoid a biological contamination risk to the patient. The mating reusable transducer portion, which is not in direct contact with the patients' blood, is frequently wiped down with alcohol or placed in a chemical sterilant after each use and then reassembled to a new, sterile dome for subsequent uses. In the late '70s, several physiological pressure transducers systems were developed using semiconductor strain sensors, but still employing a mechanical linkage and a metal diaphragm, for example the Statham P50 and the Bentley M800. The strain sensing element is a silicon beam which is bonded to the transducer body in such a way that strain is applied to the beam when the diaphragm is flexed. In these designs, the Wheatstone bridge was ion-implanted directly into the silicon beam and the output signals were calibrated using discrete resistors located in the transducer's electrical interface connector. In other respects, these "transitional" art transducers were typically connected to catheter/manometer fluid systems in the same manner as described above.

In the early '80s, non-reusable (disposable) transducers were developed using improved semiconductor strain gauges made from a silicon chip containing an etched diaphragm used in combination with laser-trimmed thick film resistor network for temperature and span compensation of the sensor chip, as is fully described in U.S. Pat. Nos. 4,576,181, and 4,291,702, 4,557,269, 4,683,894, 4,679,567, 5,042,495, 4,776,343, 5,097,841. Further, the development of thin film "on-chip" compensation methods at Motorola (see U.S. Pat. No. 4,465,075) allowed the development of even smaller, simpler disposable transducer designs as are more fully described for example in U.S. Pat. Nos. 4,539, 998, 4,679,567, and 4,825,876. Importantly, all of these disposable transducer designs except those of Cole and Kodama appear to have abandoned the mechanical linkage in favor of a hydraulic pressure coupling medium comprised of a silicone elastomer, or "silicone gel", for example as cited in U.S. Pat. No. 4,529,789. These elastomers, which had become common in the semiconductor industry for protecting chips from ambient fluids and vapors, are used to form a good electrical barrier between the chip and the saline solution, while imparting greater mechanical ruggedness and over-pressure characteristics to the sensor, plus transmission of the hydrodynamic signal. In medical use, the gel is juxtapositioned between the catheter flush solution and the transducer chip, thus conveying the hydraulic pressure signal directly to the chip's integral sensing diaphragm while isolating it electrically from the conductive and corrosive effects of the saline solution. The entire transducer assembly, including the chip are typically sold to be discarded after a single use, since the internal components can not be adequately cleaned for resterilization or reuse.

Disposable transducer designs employing semiconductor strain gauge sensors and gel coupling media as just described are desirable because they provide a relatively straight fluid channel which is easy to fill with sterile saline without turbulence or accumulation of bubbles. Further, they do not require twist-on attachment of a separate disposable dome as the prior art re-usable designs do, and they are highly rugged and accurate due to the gel pressure transmission media and silicon chip micromachined sensor structure. However, manufacturing costs remain high. The single highest cost component is the pre-calibrated semiconductor chip and associated wiring, which typically must be discarded after a single use.

With the objective of further reducing medical costs and medical wastes, accordingly, there is a need for a re-usable physiological pressure transducer which employs an inexpensive semiconductor strain gauge sensor which has been produced by current high volume silicon micro-machining and chip carrier production techniques. Wallace (U.S. Pat. No. 4,610,256) and Frank (International Application PCT/ US85/01957) disclose pressure transducers employing thick-film trimmed silicon strain gauge sensors attached to a transducer body filled with silicone oil. The exterior of the transducer body carries a pressure sensitive area covered by a flexible diaphragm which communicates hydraulic signals to the chip sensor through the silicone oil-filled body and through a hole filled with a pressure transmissive fluid which is respectively gel or oil to an opposing exterior surface. In these designs, the silicon chip sensor and compensation circuitry is carried by an exterior opposed surface of the transducer body. In both of these examples, the mating disposable dome contains a flexible sterile isolating diaphragm according to the disposable dome prior art which is intended for one time use. Adams, et al. (U.S. Pat. No. 4,686,764) discloses a gel-filled pressure transducer body containing a thin film-trimmed chip sensor. The silicon chip sensor is located inside the body and the pressure sensitive area on the exterior of the transducer consists of a flexible polymer membrane such as polyamide which transmits the hydraulic pressure signal through the gel and thus directly to the sensor without need for a coupling channel. Frank (U.S. Pat. No. 4,920,972) discloses a blood pressure transducer comprising a gel-filled body with a chip sensor again located on the outside of a body and hydraulically coupled to the diaphragm through a tapered hole filled with gel. The transducer diaphragm covering the pressure sensitive area on the opposing side of the body is a flexible material such as silicone rubber. A disposable dome of the prior art type using a flexible interface membrane is used to isolate the sterile saline from the transducer.

In spite of these improvements, nonetheless, the prior art transducers still suffer from certain drawbacks. The disposable transducers remain expensive to produce because of the high cost of throwing away the micromachined chip and wiring. The diaphragm of the earlier prior art re-usable transducers disclosed by Wallace and Frank can be easily punctured resulting in leakage of the pressure transmitting medium and failure of the transducer. While the re-usable transducers as later disclosed by Adams and Frank offer a significant improvement in mechanical ruggedness because of the use of silicone gel as the hydraulic coupling medium, the fluid path inside the dome is tortuous and still more difficult to setup, fill and de-bubble because the membrane-type dome is large in relation to the diameter of the inlet and outlet ports, and it must be attached and filled with saline prior to use. In practice, small bubbles often attach themselves in the sharp corners adjacent to the edges of the diaphragm, thus reducing the dynamic response of the transduced pressure signal.

Therefore, it would be highly desirable to develop a disposable dome for a reusable transducer application employing a fluid path without sharp corners, for instance, in the vicinity of the diaphragm, where bubbles are easily entrapped in current designs. It would also be highly desirable to develop a disposable dome structure for a re-usable transducer which has a more-or-less straight through fluid filling path to minimize the time and difficulty required to clear the system of air bubbles. It would also be desirable to reduce manufacturing cost and complexity of the medical reusable transducer design by placing the sensor chip directly inside the transducer body in communication with pressure hydraulic transmitting medium. And finally, in the prior art devices of the re-usable type, there is no physical barrier to prevent the medical practitioner from touching the non-sterile parts of the transducer while attending to the patient. It would be highly desirable to develop a means for isolating the non-sterile (reusable) parts from the sterilized parts normally manipulated by the medical practitioner during blood drawing and readjustment and calibration of the catheter and monitoring system components. These and other objects and advantages of the present invention will be apparent from the attached drawings and the description of the preferred embodiments which follow.

SUMMARY OF THE INVENTION

There is provided in accordance with one aspect of the present invention a blood pressure monitoring assembly having generally a reusable pressure transducer portion and a one time use disposable dome for sterile exposure to a patient. The assembly comprises a housing. The housing is provided with an inlet and an outlet port having a fluid flow path extending therebetween. A cavity in the flow path is divided into a first and second chamber by flexible electrical isolating and pressure transmissive medias. The flow path provides communication between the first chamber within the housing and the inlet and outlet ports.

The first chamber contains an isolating media, which transmits hydraulic pressure from fluid in the fluid flow path to the transducer. The isolating media also forms an electrical and biological barrier between the fluid flow path and the reusable transducer portion described next.

The second chamber contains a compensated pressure sensor spaced from the pressure sensitive surface with one side of the pressure sensor sealingly disposed in communication with a vent hole on an interior surface of the transducer housing. The vent hole provides an ambient air pressure reference to a first side of a pressure sensor. A pressure transmissive media is disposed in the second chamber for transmitting hydraulic pressure signals from the pressure sensitive surface to a second side of the pressure sensor. An electrical conductor is connected to the pressure sensor and extends through the housing for connection to an external blood pressure monitoring display.

The housing is divided into a first and a second removably securable components. The first component contains the first chamber, the isolating media and the inlet and outlet ports, and is adapted to be removable and disposable after a single use. The second component contains the pressure sensor, the electrical conductor, and the pressure transmissive media. In one embodiment, the first component has at least a first interference engagement surface for providing a releasable interference "snap" fit with at least one second, complementary interference engagement surface on the second component.

Preferably, the isolating media comprises a silicone gel. In a preferred embodiment, the isolating media and the pressure transmissive media are brought into direct or indirect pressure transmitting contact with each other when the first and second components are secured together. To minimize the risk of adhesion and transfer of gel upon disassembly in the case of direct contact between the isolating media and the pressure transmissive media, the isolating media and pressure transmissive media are preferably made from different materials. Alternatively, a diaphragm is provided to separate the isolating media from the pressure transmissive media when the first and the second components are removably secured together.

In accordance with another aspect of the present invention, there is provided a method of making a disposable dome for use with a reusable transducer. The method comprises the steps of forming a housing having fluid inlet and outlet ports with a fluid flow path extending therebetween. An isolating media is placed in the housing, such that it has a first surface exposed to the fluid flow path. The isolating media provides a pathway for transmitting hydraulic pressure signals from fluid in the fluid flow path through the isolating media to a second surface on the isolating media.

A releasable connector structure, such as complementary threads, snap fit, luer, interference fit, press fit or others known in the art is provided on the housing for releasably connecting the housing to a reusable transducer portion. The releasable connection between the housing and the reusable transducer is such that the second surface of the isolating media is placed in hydraulic pressure communication with the transducer.

In a preferred embodiment, the method comprises the additional step of forming the second surface of the isolating media into a convex shape in the area where it transmits hydraulic pressure signals to the reusable transducer. The isolating media may be formed by placing a curable elastomer precursor in the housing in contact with the fluid flow path to form the isolating media, and curing the elastomer precursor in place to produce an isolating media.

In accordance with a further aspect of the present invention, there is provided a method of monitoring blood pressure in a patient. The method comprises the steps of providing a patient having a catheter in communication with a blood vessel within the patient. A one time use disposable dome is provided, said dome having a housing, a flow path through the housing and a hydraulic pressure signal transmitting media placed in the housing between the flow path and a pressure signal transmitting surface exposed to the outside of the housing.

A pressure transducer having a pressure signal receiving surface thereon is further provided. The pressure signal transmitting surface on the housing is removably placed in pressure signal transmitting contact with the pressure signal receiving surface on the transducer. The flow path is placed in fluid communication with the patient by way of the catheter, and blood pressure signals detected by the transducer are measured.

Additional embodiments of one time use disposable domes, in combination with or separate from reusable pressure transducer assemblies are also disclosed.

Further features and advantages of the present invention will become apparent from the detailed description of preferred embodiments which follow, when considered together with the attached drawings and claims.

DETAILED DESCRIPTION

Figure 1:
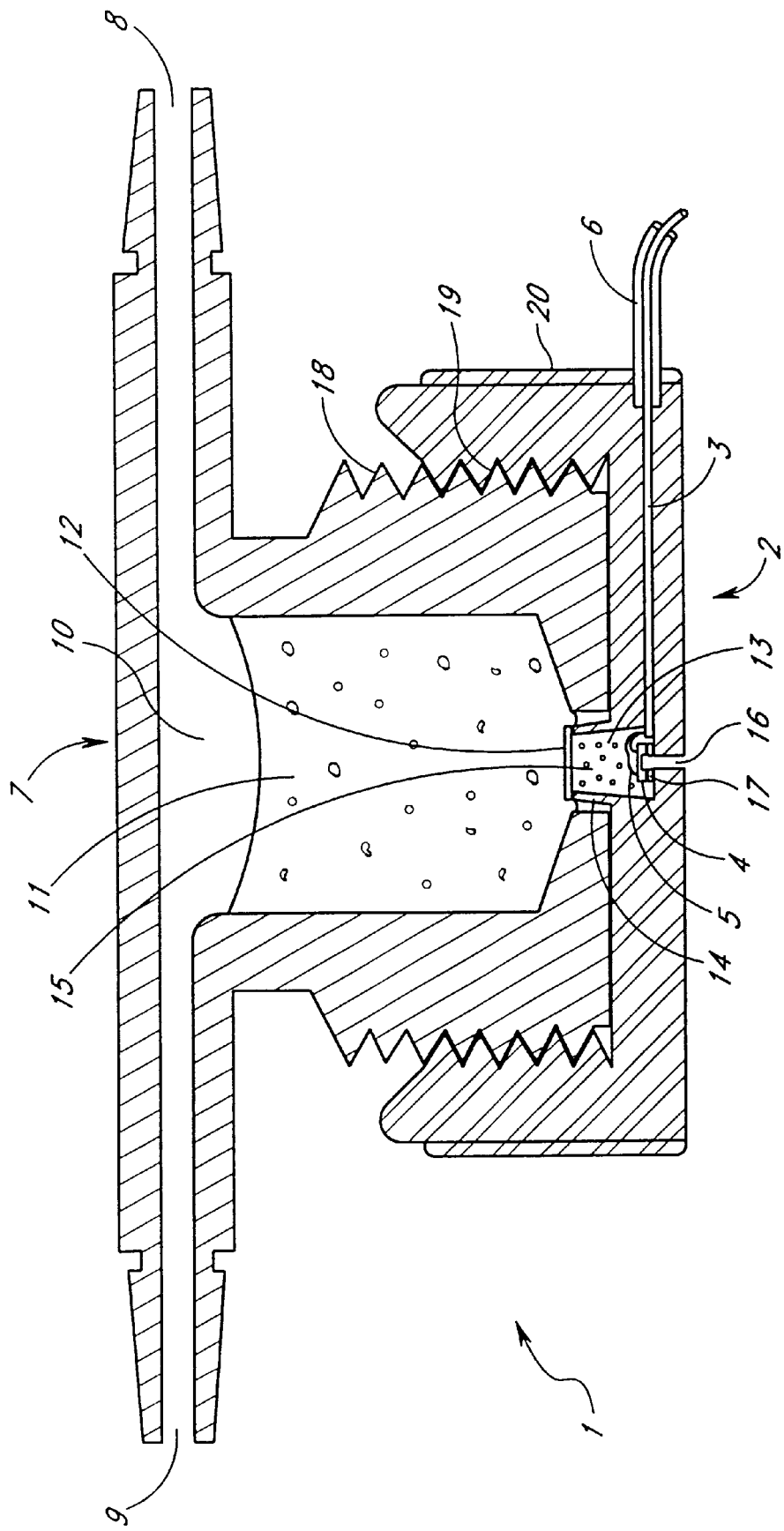
FIG. 1 is a simplified cross-sectional side view of an embodiment of the transducer assembly according to present invention taken along the centerline of the fluid inlet and outlet ports.

FIG. 1 shows a first embodiment of the pressure transducer assembly, generally denoted by the numeral 1. The assembly consists of two major parts, each with sub-parts which are mechanically connected together to form the transducer assembly 1. A first major part is the re-usable portion, generally denoted by numeral 2. Molded into the re-usable portion 2 are four electrical conductors 3, which convey electrical signals to and from the pressure sensor chip 4 through wirebonds 5. The electrical conductors carry insulating jackets 6, such that the electrical signals can be conveyed away from the transducer assembly to a remote pressure monitor (not shown) without risk of shocks or shorts.

A second major part of the pressure transducer assembly is the disposable dome 7, which is detachable from the re-usable portion 2 and generally intended for one time use. The inlet fluid port 8, and outlet fluid port 9 are in fluid-flow communication with a first chamber 10 located inside the dome 7. The dome 7 contains a pressure-transmissive, but electrically and biologically isolating gel 11 in first chamber 10 which on a first side is in contact with the flushing fluid filling said first chamber and said inlet and outlet ports, and additionally a second side of the gel is in contact with a diaphragm 12 covering a second chamber 13 both of which are part of said re-usable portion 2.

The diaphragm 12 is bonded to a raised annular ring 14 surrounding a recessed surface of the re-usable portion 2.

The diaphragm is responsive to hydraulic pressure signals transmitted through the isolating gel 11 from the fluid filling the first chamber 10. The diaphragm 12 thus conveys the hydraulic pressure signals into said second chamber 13, and then via pressure transmitting medium 15 to the pressure sensor chip 4. A pressure sensing surface of pressure sensor chip 4 is exposed to the pressure transmissive medium inside of the second chamber 13. Preferably, the on-chip circuitry for the pressure sensor chip 4 includes predetermined gain and temperature compensation. In the illustrated embodiment, the chip 4 is sealingly attached to the floor of second chamber 13 disposed over vent hole 16 using a silicone rubber sealant 17 which is applied to the floor of the recessed surface on the re-usable portion 2 in a sealing ring surrounding the end of the vent hole at it's upper-most point proximate to the chip. Contrary to the teaching of the prior art medical reusable transducers, the hole is filled with ambient air and is intended to provide a continuous ambient reference pressure to one side of the sensor's internal diaphragm for proper referencing of the patient's fluid pressure measurements to ambient pressure.

A threaded cylindrical portion 18 of the dome is releasably engaged into a mating threaded portion 19 of the re-usable portion when the two major portions 2 and 7 have been assembled for use. Friction enhancing structures such as a plurality of axially extending raised ribs 20 on the outer surface of the re-usable portion 2 allow the re-usable portion to be grasped and turned in relation to the inlet and outlet ports 8 and 9 for assembly and disassembly of the pressure transducer assembly 1.

Figure 2:
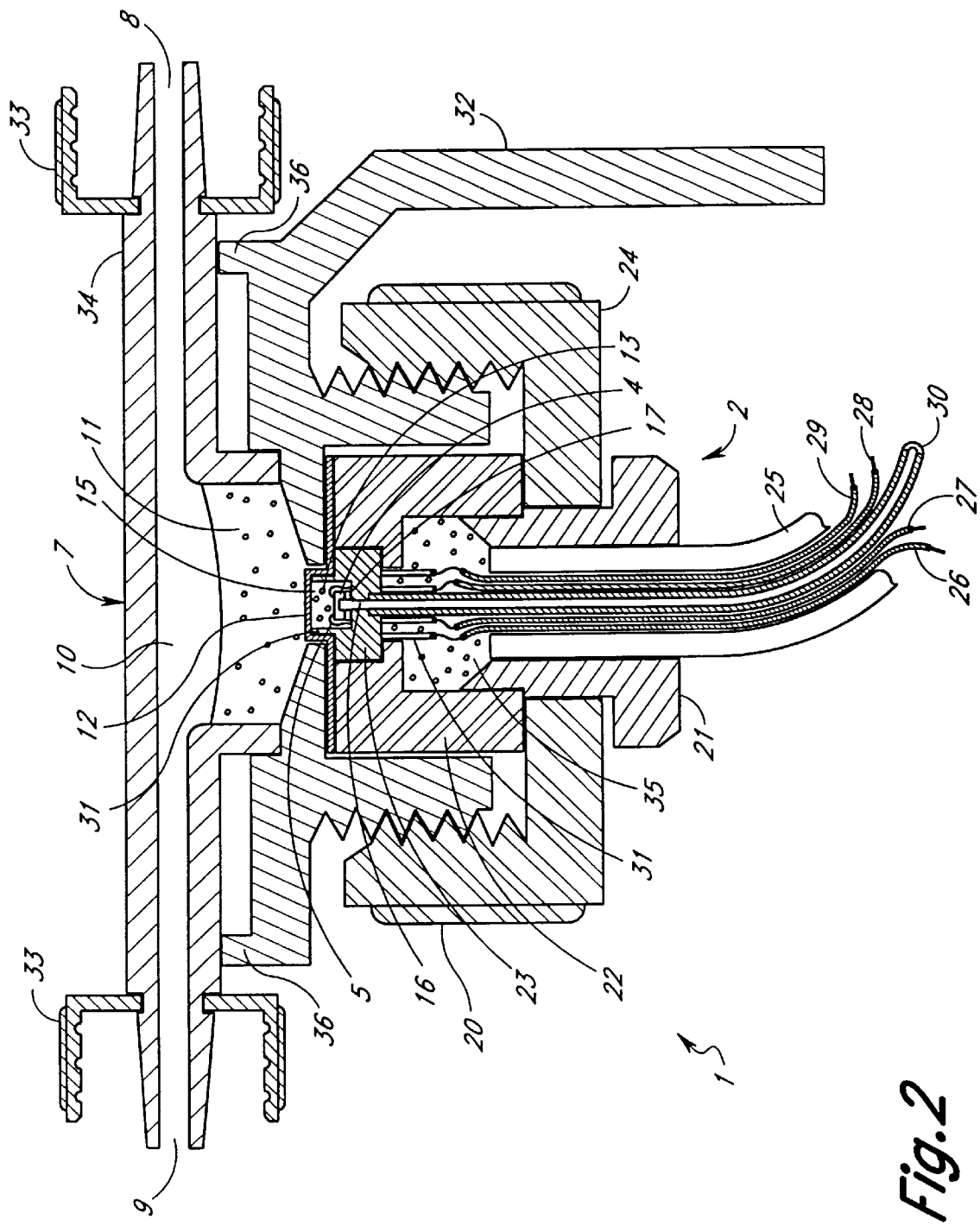
FIG. 2 is a cross-sectional view of a first preferred embodiment of the transducer assembly, again taken along the centerline of the fluid inlet and outlet ports.

FIG. 2 is a cross-sectional view of another embodiment of the transducer assembly as generally denoted by the numeral 1, again taken along the centerline of the fluid inlet and outlet ports 8 and 9. The re-usable portion as generally denoted by the numeral 2, includes a hub formed from elements 21 and 22. Rotating nut 24 is rotatably carried in an annular channel formed in the hub. Rotating nut 24 is provided with a plurality of radially inwardly facing annular threads for releasably engaging the corresponding threads on the disposable dome 7. Any of a variety of alternate releasable retention structures can be used as will be apparent to those of skill in the art, as long as the structure selected provides a sufficient compression to produce an adequate propagation of the pressure signal across the interface between media 15 and 11.

The re-usable portion 2 further includes a cable jacket 25 containing four insulated electrical conductors 26, 27, 28, 29 and sensor vent tube 30 (which is shown in cross section). The insulated electrical conductors 26–29 have their insulation removed at their ends terminating inside the re-usable portion 2, and the tinned ends of said conductors are soldered to sensor housing pins 31. To prevent shorts and increase fluid and corrosion resistance, the area generally denoted by the numeral 35 is preferably filled with a potting compound such as silicone rubber. The sensor housing pins at their upper ends are molded into sensor housing 23, and terminate inside of second chamber 13, wherein they are connected to wirebonds 5. The wirebonds are connected to aluminum or gold pads on the pressure sensor chip 4, as is well known in the art. Thus the electrical signals are conveyed to/from the pressure sensor chip through wirebonds 5, sensor housing pins 31, and insulated electrical conductors 26–29, and thusly to an external electrical interface connector, pressure amplifier and measurement display system (not shown). The pressure sensor chip 4 is sealingly attached to the interior surface of second chamber 13 using a silicone RTV 17, disposed over a vent hole 16, which is in communication with vent tube 30. Thus, the air channel formed by vent hole 16 and vent tube 30 provides a continuous ambient reference to a first side of the sensor's internal diaphragm for referencing of the patient's fluid pressure measurements to ambient atmospheric pressure. Second chamber 13 is filled with a pressure transmissive media 15, such as silicone oil, or preferably a cross-linked poly-dimethyl siloxane, for instance a platinum cure, two part silicone gel available from Rhone-Poulenc Visalox V-191.

A disposable dome portion generally denoted by numeral 7 of the transducer assembly 1 consists of a clear molded portion 34, incorporating inlet and outlet fluid channels 8 and 9, in fluid flow communication with a first chamber 10, located inside the clear molded portion, a pressure transmissive but electrically and biologically isolating gel 11 disposed in a recess in said first chamber, a threaded support plate 32, and rotating luer nuts 33. The rotating luer nuts provide a means of securely connecting the inlet and outlet ports to fluid transmission tubing and a fluid-filled catheter inserted in a living body. The clear molded portion 34 is preferably molded of a clear plastic material such as polycarbonate so that any bubbles or blood located in the fluid filling said first chamber 10 or said inlet and outlet fluid channels 8 and 9 can be easily observed and removed during the fluid filling setup process, as is well known in the art.

During manufacturing of the disposable dome portion 7, the clear molded portion 34 is ultrasonically welded, or solvent or adhesive bonded to the threaded support plate 32. The lower portion of the chamber thus formed (the first chamber 10) is filled with the isolating gel in an uncured state and the gel is cured and contoured to form isolating gel 11 as shall be fully described in conjunction with the description of FIG. 5.

The isolating gel 11 is located between said fluid and said diaphragm 12, and thus provides an electrical and biological barrier between said fluid which is in communication with an invasive catheter, and the diaphragm 12, which presents a pressure sensitive surface on the re-usable portion 2. Diaphragm 12 is sealingly attached to an annular ring which forms an upper extension of second chamber 13, spaced from re-usable portion 2. For additional mechanical ruggedness and fluid resistance, the diaphragm is preferably a pressure formed polymer or rubber sheet and further extends across the entire upper surface of the re-usable portion 2 where it contacts disposable dome portion 7. The diaphragm is preferably made of a material such as 2–10 mil thick polyisoprene, but it can also be formed from 302 stainless steel, nitrile or butyl rubber, high density polyethylene, Dupont Mylar, Teflon, or polyamide sheet, such as is sold under the brand name Capton® or Upalon®.

Alternately, two dissimilar materials may be selected for said isolating and said pressure transmitting medias such that the two materials do not bond to one another during normal periods of contact in actual use. In such case, the pressure transmitting medium could also form an integral diaphragm means. This alternate embodiment of diaphragm 12 has been demonstrated by partially filling chamber 13 with a pressure transmitting medium such as cross-linked poly dimethyl siloxane, followed by a top layer of a single component primerless Dow silicone adhesive; Catalog No. 3-6611. Once cured, the silicone adhesive sticks to the pressure transmitting medium and forms a tough outer skin which is integral membrane 12. The cured adhesive is sufficiently different in composition and hardness from isolating gel 11 that it can be used to contact the isolating gel 11 directly. Additional surface modifications of the pressure transmitting medium are also possible, such as electron beam deposition of an evaporatable metal such as silver in a vacuum to form a hardened and dissimilar surface which nonetheless is still effective in transmitting hydraulic pressure signals.

As stated, the second chamber 13 is preferably filled with a pressure transmissive medium 15 such as a silicone gel. In the event the diaphragm 12 is chosen from a material that is light transmissive, the silicone gel can include a filler such as carbon black in powder form which renders the pressure transmissive medium non-light transmissive as is well known in the art. Thus, light is prevented from entering the second chamber to affect the pressure readings produced by the pressure transducer chip 4.

In clinical use, the pressure transducer assembly 1 is easy to assemble from re-usable portion 2 and disposable dome portion 7. The re-usable portion, with it's pressure sensitive diaphragm 12 facing forward most, is advanced into the recess formed in the lower portion of the threaded support plate 32. As the re-usable portion is advanced, rotating nut 24 engages the mating threads of the support plate. Then the rotating nut is rotated a number of turns to fully advance the diaphragm 12 into contact with the isolating medium 11. During the advancement process, any air contained between said diaphragm and said isolating medium is allowed to escape in the crevasses formed between the mating of said re-usable and disposable dome portions. As the diaphragm 12 contacts the isolating medium 11 firstly at the diaphragms' center as shall be more fully described in conjunction with FIG. 5, the isolating gel medium flows and deforms back in a controlled and uniform manner into the first chamber 10 to fully eliminate any remaining air between said diaphragm and said isolating medium, said remaining air escaping through the crevasses between said re-usable portion 22 and the recessed portion of support plate 32. To prevent the diaphragm 12 from rotating and possibly upsetting the smooth and uniform contact with the isolating gel 11, the interior recess in support plate 32 which accepts the mating re-usable portion 22 can be optionally constructed in a non-round shape, or a guide channel and mating keyway can be molded into the subject mating parts to rotationally link hub component 22 with respect to the gel 11.

Figure 3:
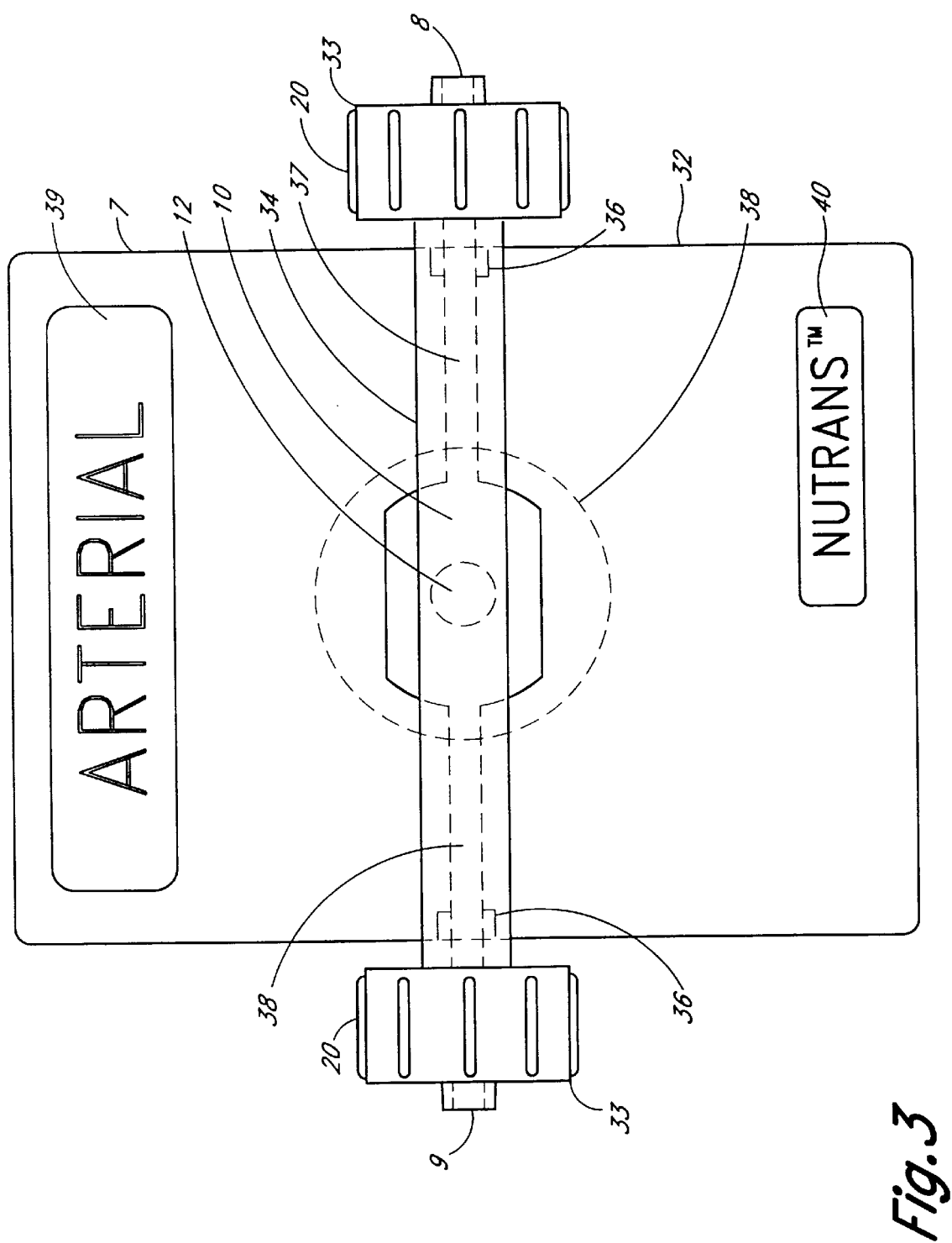
FIG. 3 is a front view of the transducer dome according to the present invention prior to connection to a flush device, fluid-conducting tubing, or catheter.

In FIG. 3 is shown a front view of disposable dome portion 7 of the first preferred embodiment of the invention, showing the clear molded portion 34 of the dome, the topside of threaded support plate 32, inlet port 8, outlet port 9, first chamber 10, rotating luer nuts 33, raised ribs on luer nuts 20, support lands 36, diaphragm 12 (seen through clear molded portion of dome and isolating medium 11), fluid inlet channel 37, fluid outlet channel 38, a hidden view of the threaded portion of the support plate 38, molded land areas 39 and 40 for attachment of self-adhesive labels.

Support plate 32 is molded of a non-transparent material such as colored polycarbonate, styrene or ABS. A clear molded portion 34, containing the inlet and outlet fluid channels 37 and 38 and rotating luer nuts 33 is affixed to the top surface of the support plate, forming first chamber 10. Support lands 36 provide extra mechanical support for the clear molded lumens surrounding the inlet and outlet channels 37 and 38 as they exit the sides of the support plate. To improve the appearance of the support plate 32, the surface is preferably textured. Land areas 39 and 40 may be defined by small ridges or grooves along their borders and a smooth surface finish within. Labels may be added to these land areas during clinical setup of the pressure transducer assembly to designate the specific measurement function and catheter being used with the invention, and/or to place product brand name labels.

From the drawing of FIG. 3, it is easy to see that the transducer assembly according to the present invention can be used with the inlet and outlet channels 37 and 38 in either a horizontal or vertical position with the appropriate mounting brackets. For easy filling and de-bubbling in the ICU or Operating Room, it is often preferred to place the fluid channels in the vertical position, as is more fully described in FIG. 9. However, in the catheterization laboratory, where several transducers will be daisy-chained together with interconnecting stopcocks located in between each transducer to accommodate connection and filling of multiple catheters, i.e. in a manifold configuration, it is often more desirable to locate the inlet and outlet channels 37, 38 in the horizontal orientation. The invention is intended to accommodate both applications.

Figure 4:
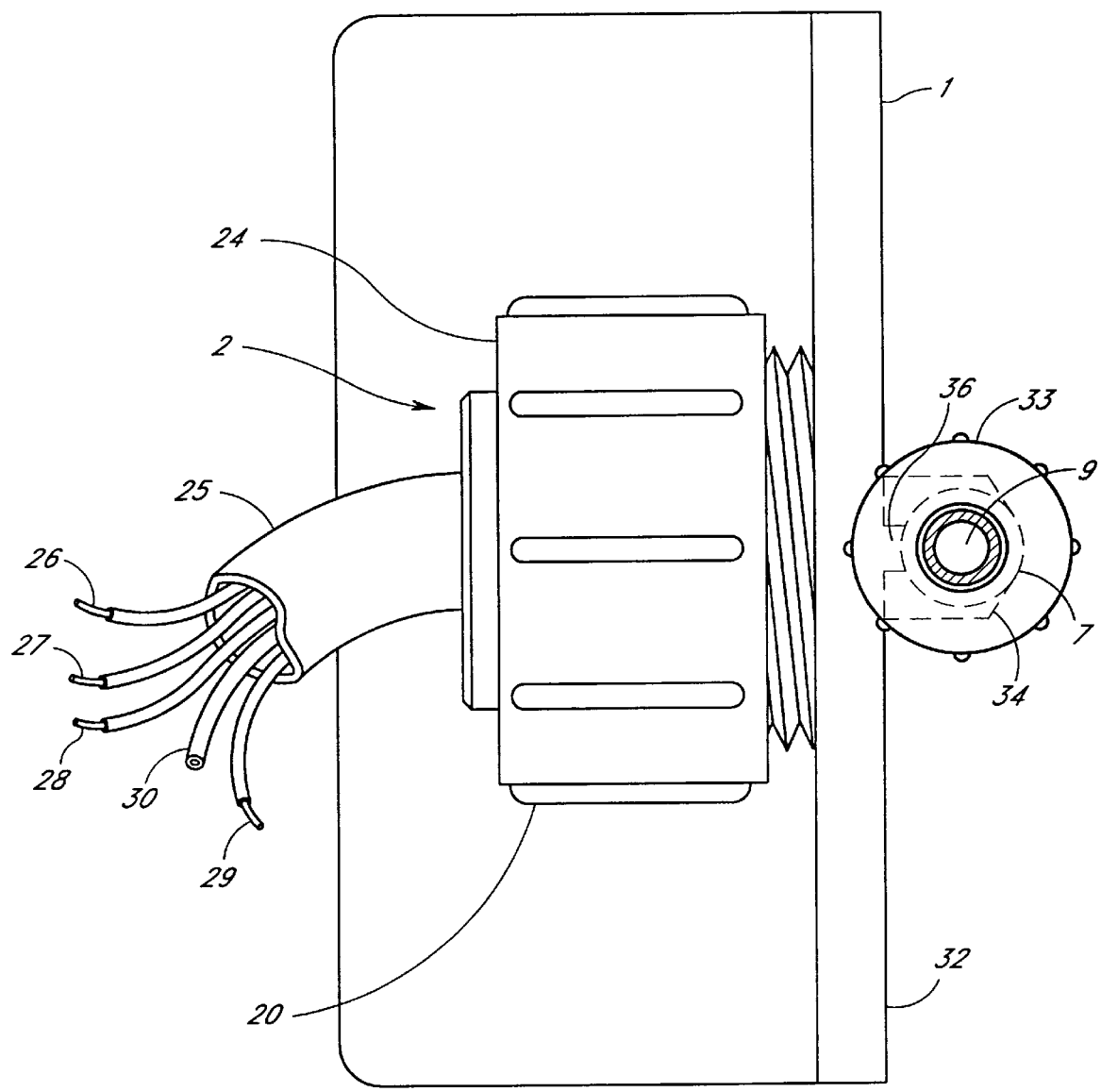
FIG. 4 is a top view of a transducer assembly according to the present invention, showing a side view of the dome of FIG. 3, to which the transducer has been installed.

FIG. 4 is a top view of the first preferred embodiment, showing the threaded support bracket 32, a re-usable portion generally denoted by the numeral 2, rotating nut 24, ribs 20, cable jacket 25, insulated electrical conductors 26–29, vent tube 30, rotating luer nut 33, outlet port 9, and hidden views of the clear molded portion 34 of the dome and support land portion 36 of the support bracket.

As can be seen from this illustration, the molded support bracket 32 effectively provides a physical barrier between the clear molded portions of the disposable dome 7 and the re-usable portion 2. Any sterile tubing, catheter, or flush device components are intended to be installed to the disposable dome, with the molded support bracket serving as a sterile shield placed between such components and the re-usable portion 2. The lower extension of the threaded support bracket, as seen in this Figure as extending underneath the re-usable portion 2, is intended to be secured to an IV pole using a standard pole mount manifold clamp, as is well known in the art (for example, see FIG. 9). Once the transducer assembly 1 has been installed on an IV pole using a suitable clamping bracket attached to rearmost portion of the threaded support bracket 32, the tubing, flushing, and catheter components are assembled to the disposable dome portion 7, using sterile technique, without the need to touch the re-usable portion 2. The forward surface of the threaded support bracket 32 further prevents inadvertent contact with the re-usable portion during manipulation of the sterile components being attached to the disposable dome portion 7.

Figure 5:
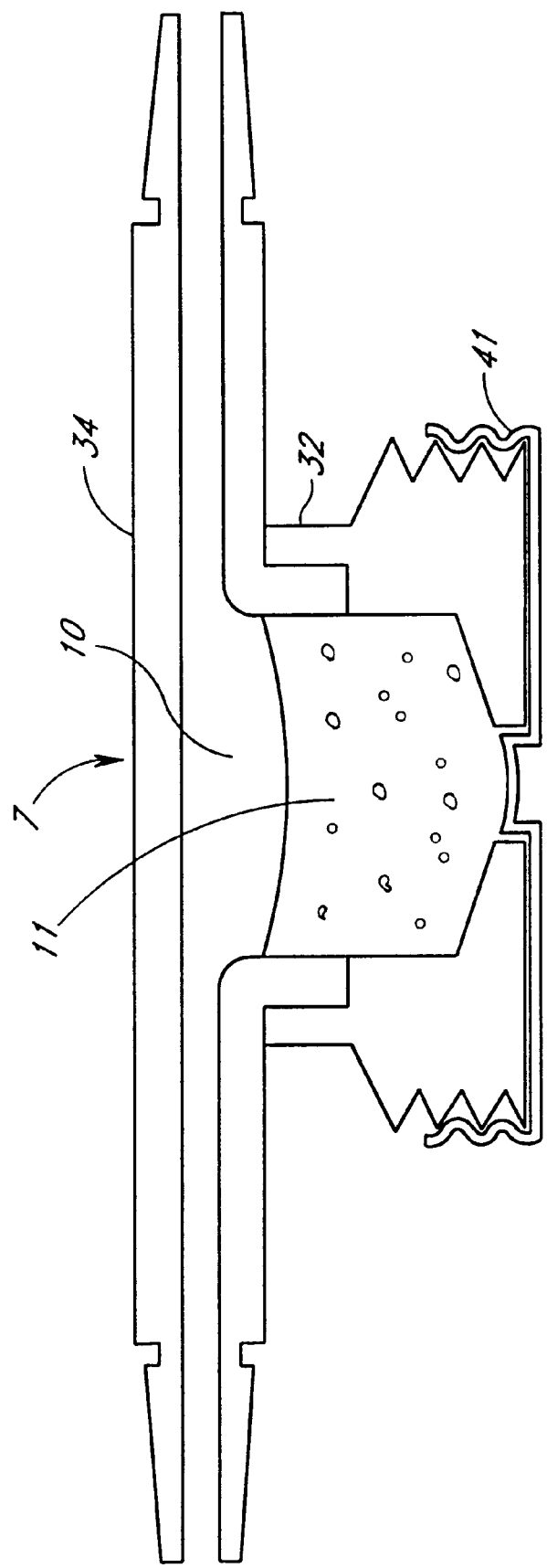
FIG. 5 is a cross-sectional view of a transducer dome according to the present invention without the transducer installed. Instead, a gel contouring "dust" cap has been installed on the dome for the purposes of curing the gel into a preset convex shape at the transducer/dome interface area.

In FIG. 5 is shown an elevational cross-sectional view of a disposable dome portion 7 according to the present invention to illustrate the process of forming the isolating medium 11. During manufacturing of the disposable dome portion 7, the clear molded portion 34 is ultrasonically welded, or solvent or adhesive bonded to the threaded support plate 32. A matingly formed dust cap 41 is inserted over the bottom end of the threaded support bracket 32 to prevent escape of fluid. The dust cap 41 provides a convex shape of the gel in the opening in the threaded support plate designed to be contacted by the diaphragm as earlier described. The lower portion of the container thus formed is filled with silicone gel in an uncured state and the gel is cured in a contoured shape to form isolating gel 11. The isolating gel 11 is a pressure transmissive but electrically and biologically isolating media, such as a cross-linked poly-dimethyl siloxane, for instance a platinum-cure, two part silicone gel available from Rhone-Poulenc as catalog # Visalox V-191. Once the gel is cured and with the dust cap in place, the disposable dome portion 7 is placed in a package and processed to produce a sterile packaged sub-part. When un-packaged for assembly by the medical practitioner onto the reusable portion, the dust cap is removed and discarded, leaving a sterile, external convex surface of isolating medium 11 presented to engage with the re-usable portion, and more specifically to engage with diaphragm 12 or other contact surface such as in an embodiment from which the diaphragm has been deleted or integrally formed.

The dust cap 41 is preferably made of pressure formable plastic material which will not adhere to curing silicone gel, such as polyethylene or plasticized PVC. The sides of the dust cap have groves designed to make an interference fit with the threads on the support plate. To provide an even tighter seal of the dust cap to the threaded support bracket 12, the dust cap can optionally be threaded on the portions contacting the threads of the support plate.

To further improve the mating of the diaphragm 12 to the isolating medium 11, the dust cap can be removed at any time after curing of the gel, and a drop of silicone oil applied to the center of the convex gel surface. This step can be performed, for instance, by briefly removing the dust cap after curing but before packaging for sterilization, applying the oil to the concave surface formed in the dust cap, then reattaching the dust cap and resuming the packaging and sterilization process as described above.

Figure 6:
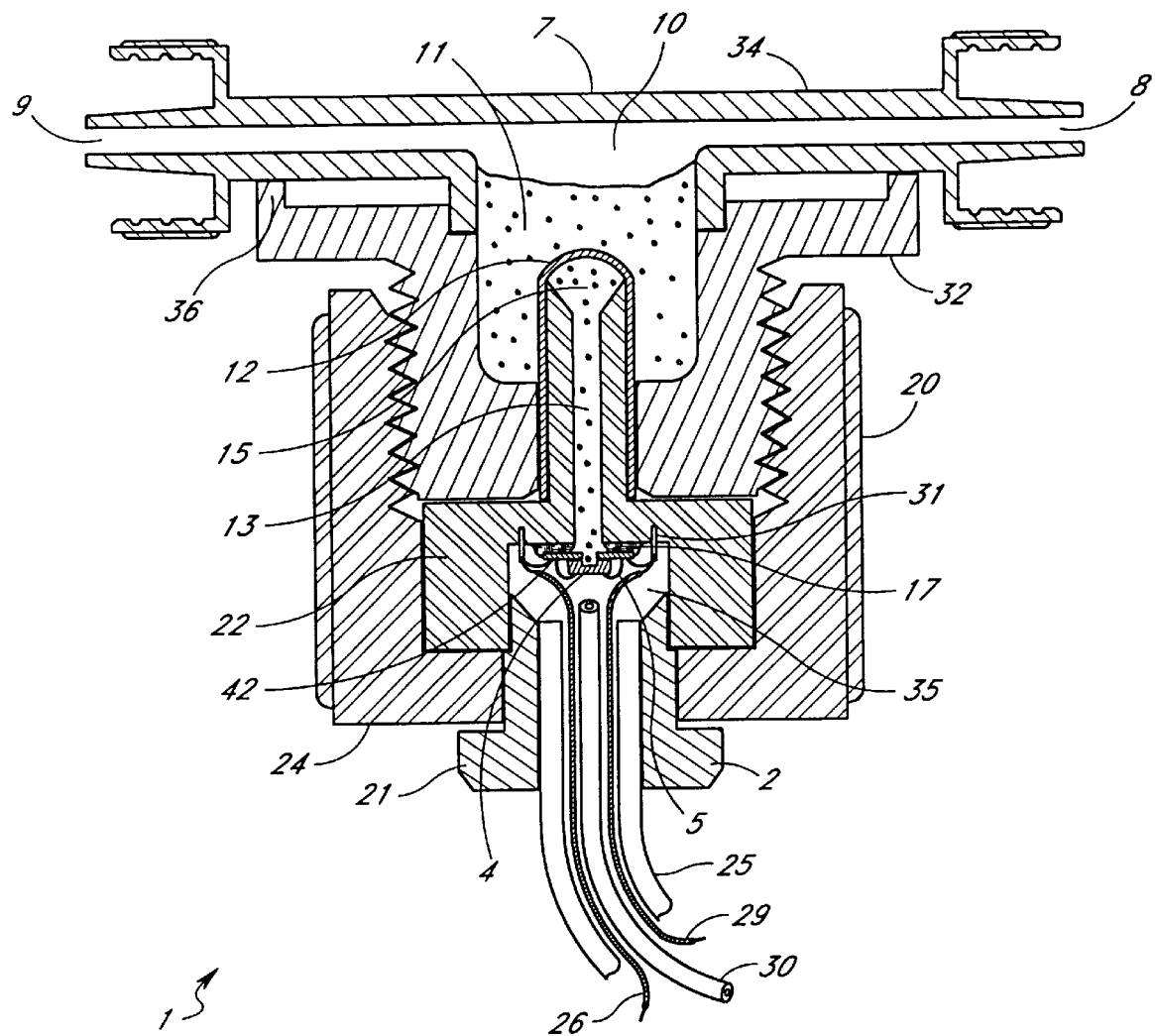
FIG. 6 is an elevational cross-sectional view taken along the centerlines of the inlet and outlet ports of a second preferred embodiment of the present invention.

In FIG. 6 is shown a further preferred embodiment 1 of the present invention in a cross-section view taken along the centerlines of fluid inlet and outlet ports 8 and 9. In this drawing, insulated electrical conductors 27 and 28 are not shown, but it shall be understood that they follow the same general direction, positioning, and course as the illustrated electrical conductors 26 and 29. Also, the rotating luer nuts 33, of the first embodiment have been replaced with fixed luer receptacles which form an integral part of the clear molded dome portion 34. Any of a variety of conventional fluid line fasteners can be used, as will be apparent to those of skill in the art.

The embodiment of FIG. 6 operates in a similar manner to the first preferred embodiment, except that diaphragm 12 is now provided with a generally spherical shape over it's active, pressure responding area. Further, more space has been provided in area 35 for placement of a thick film resistor calibrating network 42 for zero and span compensation of a chip 4 which does not contain it's own on-chip thin-film compensation. In this embodiment, the thick-film network acts as a carrier for the chip. The carrier is adhesively bonded to form the floor of second chamber 13. A pressure transmitting media 15 fills the chamber and transmits hydraulic pressure signals from pressure responsive diaphragm 12 which is in communication with isolating medium 11 and the fluid in first chamber 10, to a first side of a silicon chip sensor 4. In this embodiment, the isolating medium 11 is preferably U-shaped, with the legs of the "U" pointing away from the fluid path and in the direction of the reusable portion of the transducer. Vent tube 30 provides an ambient pressure reference to the second side of the chip sensor. The thick-film network 42 is preferably attached to the re-usable portion 22 using an annular ring of silicone rubber 17. The sensor housing pins 31 are attached into sensor housing 22 and smaller soldered leads or wirebonds extend from said sensor housing pins to the thick film substrate or directly to the chip. Thus, placement of undue stresses from the cable and insulated electrical conductors 26–29 is avoided on the thick film substrate or chip. Alternately, insulated electrical conductors 26–29 can be of a sufficiently fine gauge that the electrical conductors can be soldered directly to the thick film substrate. Or, alternately, the pins can form a spring contact to the thick film substrate 42, with the insulated electrical conductors in contact with insulation penetrating contacts which form a part of the pin, see for instance U.S. Pat. Nos. 4,230,391 and 4,825,876 the disclosures of which are incorporated herein by reference. Such variations in electrical contact means shall be obvious those experienced in the art.

Figure 7:
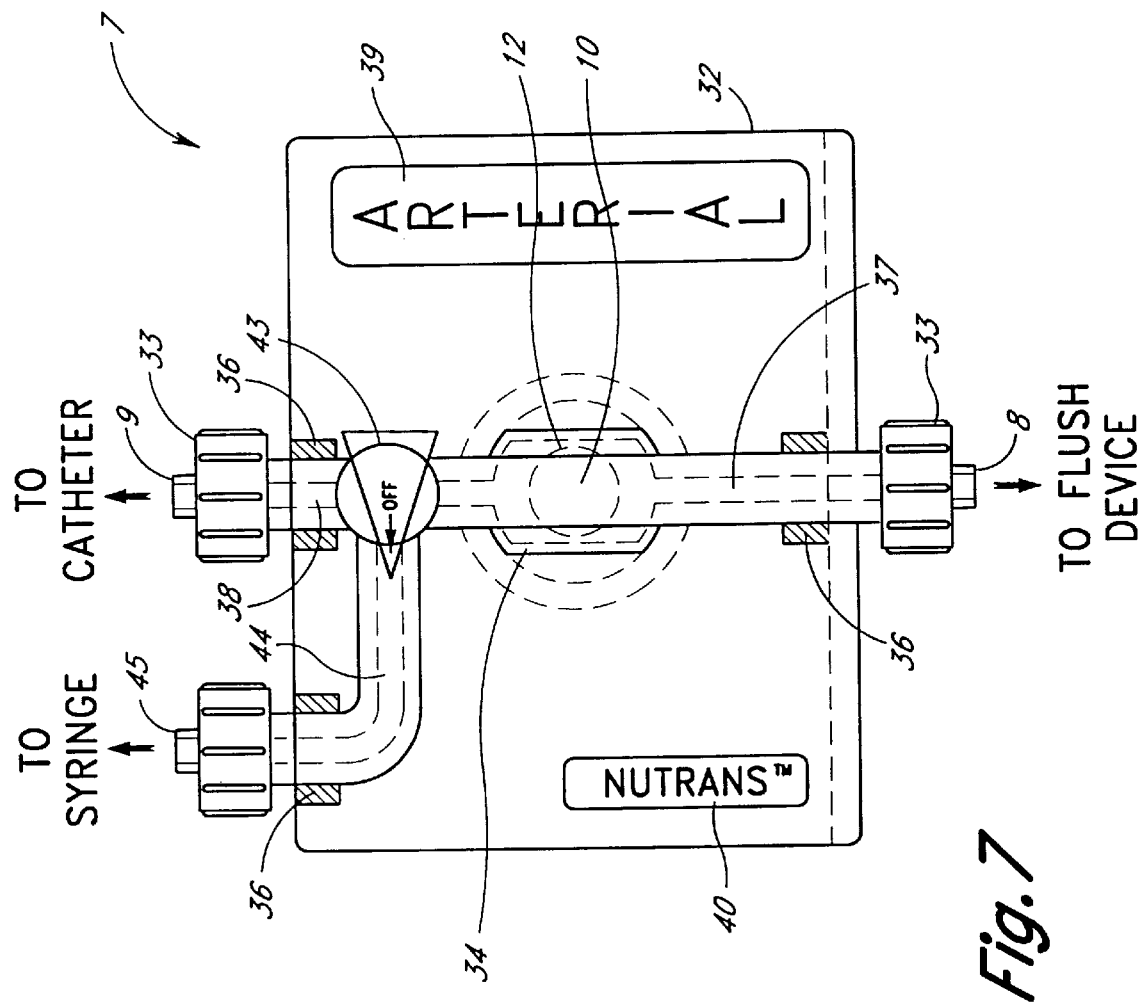
FIG. 7 is a top view of a second preferred embodiment of the disposable dome portion.

FIG. 7 is a front view of an embodiment of the disposable dome portion 7 according to the present invention, where a 3-way stopcock 43 and an auxiliary fluid channel 44 have been added to the fluid outlet path 38 of the disposable dome portion to provide for convenient manipulation of sterile fluid volume or pressures at the auxiliary outlet port 45 for more convenient zeroing, calibrating, and blood drawing as shall be now described.

Disposable dome portion 7 is typically connected at it's inlet port 8 to a flush device which is a controlled flow source of sterile saline. During setup, the flush device is used to fill the fluid inlet channel 37, the first chamber 10, the fluid outlet channel 38 and then ultimately the attached tubing and catheter. By inserting 3-way stopcock 43 in said fluid outlet channel several other functions can be performed. Stopcock 43 is shown in it's normal pressure measuring position with the stopcock's port in communication with the auxiliary channel 44 turned to the "off" or blocked position. In this position, normal fluid-fluid flow communications is allowed between the catheter and the first chamber 10. A continuous slow flow of sterile flush solution for the catheter is also supplied through the inlet port by the flush device. (In an alternate configuration, a stopcock can be placed on the inlet port 8 and the flush device can placed in series with the pressure tubing leading from the outlet port 9 to the catheter.)

When the stopcock "off indicator" on the handle is turned in the direction of the first chamber 10, pressure monitoring and flushing of the catheter is suspended, and sterile fluid in the catheter is in communication with auxiliary fluid channel 44 and auxiliary port 45. A syringe of approximately 10 CC capacity is attached to auxiliary port 45, typically with it's handle pushed fully down so that it's internal fluid volume is minimal. By pulling up on the syringe handle, with the stopcock off arrow pointing toward the transducer, the medical practitioner can withdraw up to 10 CC's of fluid from the catheter and interconnecting lines, thereby drawing blood up into the catheter and tubing for the "needle-less" collection of blood at a HEMOLOC TM site 52 just proximal to the catheter (see FIG. 9). After collection of a small blood sample at the HEMOLOC TM site, all of the remaining blood in the catheter and tube can be injected back into the patient by pushing down on the handle of the syringe. This needle-less and non-blood-spill sampling technique thus is a great advantage for reducing the risk of infection to medical personnel from inadvertent needle ("sticks") i.e. wounds to practitioners, or blood spillage in the vicinity of the patient.

Further, if the stopcock handle is turned such that the off indicator on it's handle is turned in the direction of the outlet port 9, then pressure monitoring and flushing of the catheter is suspended and the auxiliary fluid channel and syringe can be filled with sterile saline using the flush device, for instance for use in thermodilution cardiac output injections. And by temporarily removing the syringe with the stopcock handle in this position, the fluid in chamber 10 and thus the silicon chip sensor is exposed to an atmospheric or other reference pressure for zeroing or calibrating the pressure measurement system. When the auxiliary port is used for zeroing of the transducer according to the above-described method, the medical practitioner typically would locate the vertical level of the auxiliary port 45 at the mid-heart height for the most accurate calibration of the pressure measurement system to the patient's current position and posture.

Thus, addition of the stopcock 43, auxiliary fluid channel 44, and auxiliary port 45 offers distinct advantages of an easy and an accurate method of calibrating the pressure measurement system, plus an improved method of drawing blood samples for laboratory analysis while not wasting or spilling any of the patient's blood.

Figure 8:
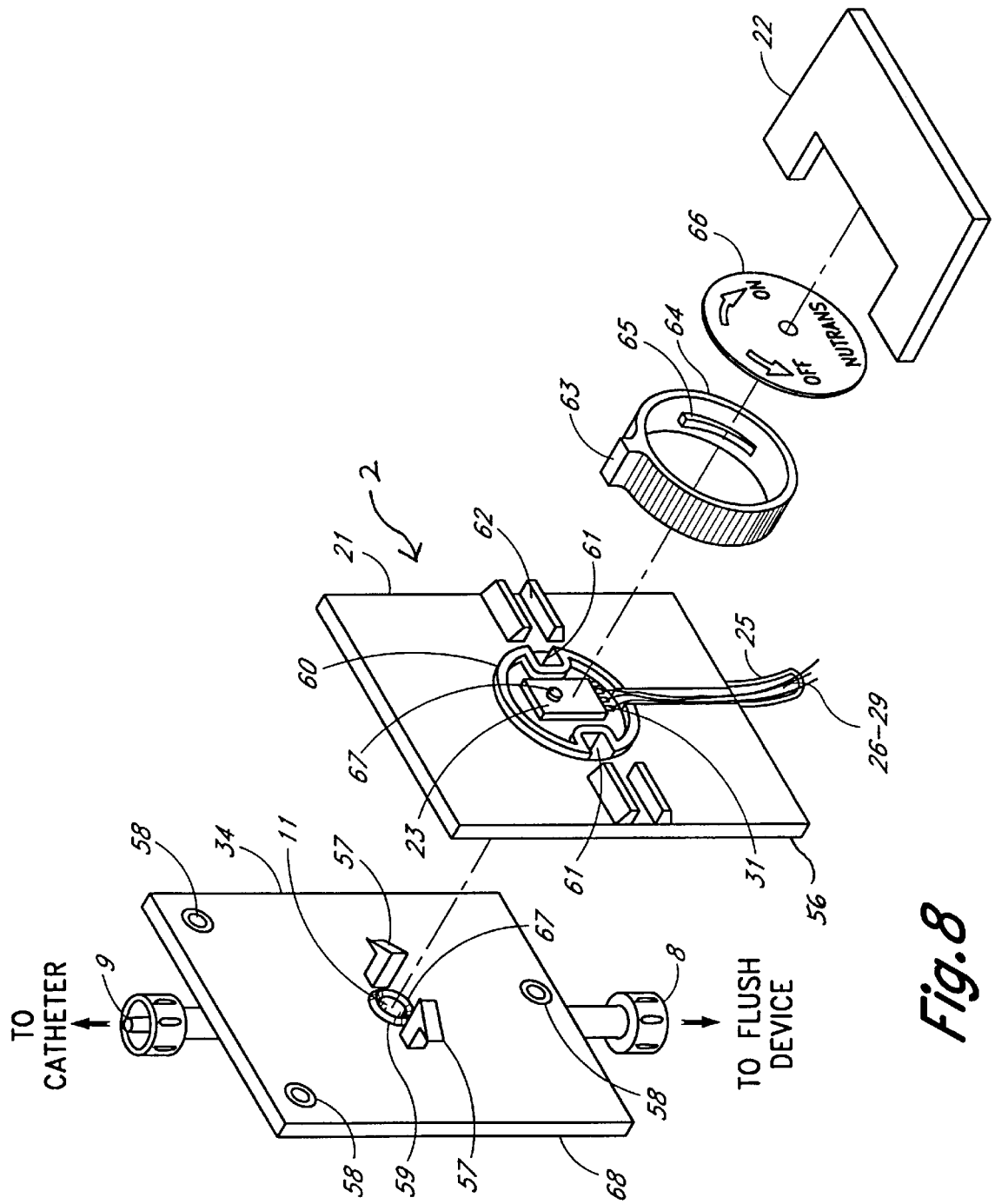
FIG. 8 is an exploded perspective view of the assembly parts comprising yet a third preferred embodiment, wherein the support plate has been made part of the re-usable portion of the transducer assembly and the clear molded dome portion includes an attachment and retention structure and sterile shield.

FIG. 8 shows an isometric view of the parts comprising yet a third preferred embodiment of the invention. In this embodiment, the support plate 56 is made part of the re-usable portion 2. The re-usable portion is assembled by first bonding the sensor housing 23 into a recessed area surrounded by a raised rim on the back side of the support plate 56. The second chamber portion of the sensor housing with it's raised rim and diaphragm passes through a hole in the support plate so that these leading portions are disposed on the front side of the plate in alignment with a mating hole 59 in clear molded portion 34.

Insulated electrical conductors 26–29 are soldered to sensor housing pins 31, and routed through a channel in the support plate to an external electrical cable 25. After the support plate, sensor housing, and insulated electrical conductors are assembled, the recessed area in the back of the support plate is preferably potted with RTV silicone rubber or epoxy to eliminate leaks and shorts, while keeping all sealant away from vent hole 67 so that it remains exposed to ambient air pressure. A clamping ring 63 is then placed over raised rim 60 in a loosely fitting arrangement so that it can rotate around the sensor housing center axis. The clamping ring contains ramps on it's inside walls which are designed to be matingly engaged with the barbs 57 on the disposable portion when the barbs are inserted into mating holes 61 and the ring is rotated clockwise. Thus the clamping ring and barbs are an engagement and retention means to draw together and hold the re-usable and disposable portions when operated as described above.

Self-adhesive label 66 is then attached to rim 64 on the clamping ring, and reusable bracket 22 is then bonded to a horizontal grove in the support plate to complete the assembly of the re-usable portion.

The mating hole 59, surrounded by raised sealing edge 67 is formed in a rear portion of said first chamber in the back of the clear molded portion 34 and the rearward convex portion of the isolating medium 11 can be seen in the mating hole 59. The clear molded dome portion, generally denoted by the numeral 34, includes two barbs 57, and three raised pads 58. As explained above the barbs form a mating and engagement means with the re-usable portion. During engagement, the raised pads 58 provide a slight displacement of the upper and bottom portions of sterile shield portion 68 away from the support plate 21. As a result, when the re-usable portions are drawn together by the engagement mechanism of the barbs 57 and clamping ring 63, a slight bending of the two mating pieces at their horizontal centers will produce a first contact in the region of hole 59 and sealing edge 67, thus assuring a firm and repeatable seal of the hydraulic pressure signal transfer path.

The sterile shield 68 prevents the medical practitioner from touching the reusable portion when manipulating the zeroing stopcock or when inspecting the seethrough portion of the dome. For cost reasons, it is intended to be constructed of thin plastics such as polycarbonate, and is preferably molded in a single step molding process during the same step where the inlet and outlet fluid channels, and clear molded portion is formed.

This third preferred embodiment has an advantage over the first two preferred embodiments for the minimization of plastic material used in the disposable portion. This feature may be of particular advantage in markets where there are restrictions and high costs for hospitals and suppliers associated with excessive use of throw away plastics materials.

Figure 9:
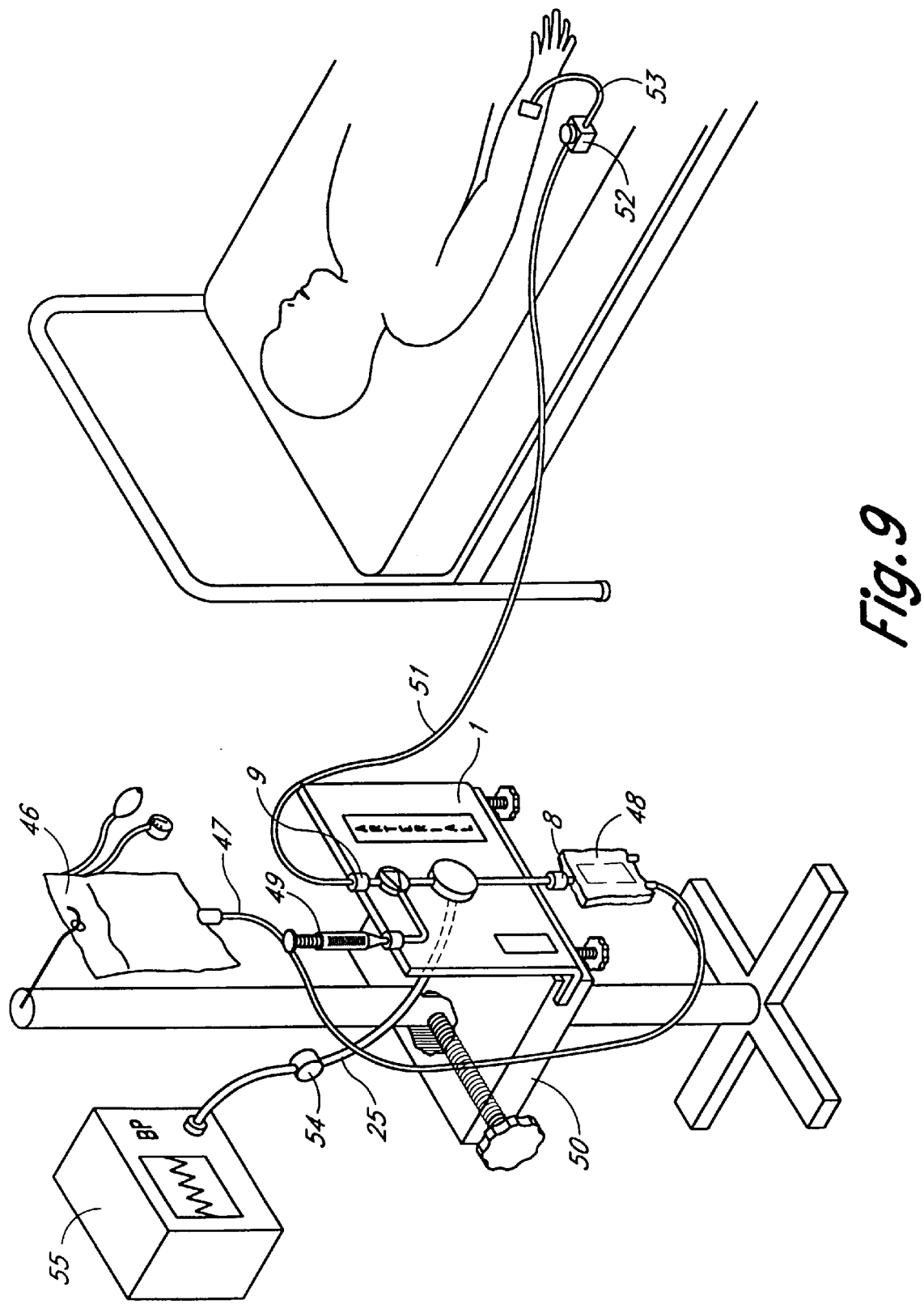
FIG. 9 is a schematic illustration of a typical pressure measuring system for fluid flushing and continuous measurement of pressures in a single catheter according to the present invention.

FIG. 9 shows an isometric view of one form of complete pressure measurement system for monitoring and maintenance of a single catheter according to the present invention, including a source of pressurized flush solution 46 which includes a plastic IV bag filled with solution, a pressure cuff, inflation bulb, and pressure gauge, an IV administration set 47 incorporating a drip chamber, a flush device 48 connected to inlet port 8 of transducer assembly 1, a 10 CC disposable syringe 49 incorporating a sterile protection boot over it's barrel and handle which is connected to auxiliary port 45, insulated electrical conductors in the cable 25 connecting to an electrical interface connector 54, said interface connector being in electrical communication with a pressure measurement and display system 55, a manifold pole mount clamp 50 attached to an IV pole and mechanically clamping a rear portion of the transducer assembly 1 in a groove in said clamp using clamp screws, a pressure tubing connecting the outlet port 9 to a HEMOLOC TM port 52, and said HEMOLOC TM being connected to a fluid tubing leading to the catheter 53 adapted for measuring a physiological pressure of interest in a living body.

Figure 10:
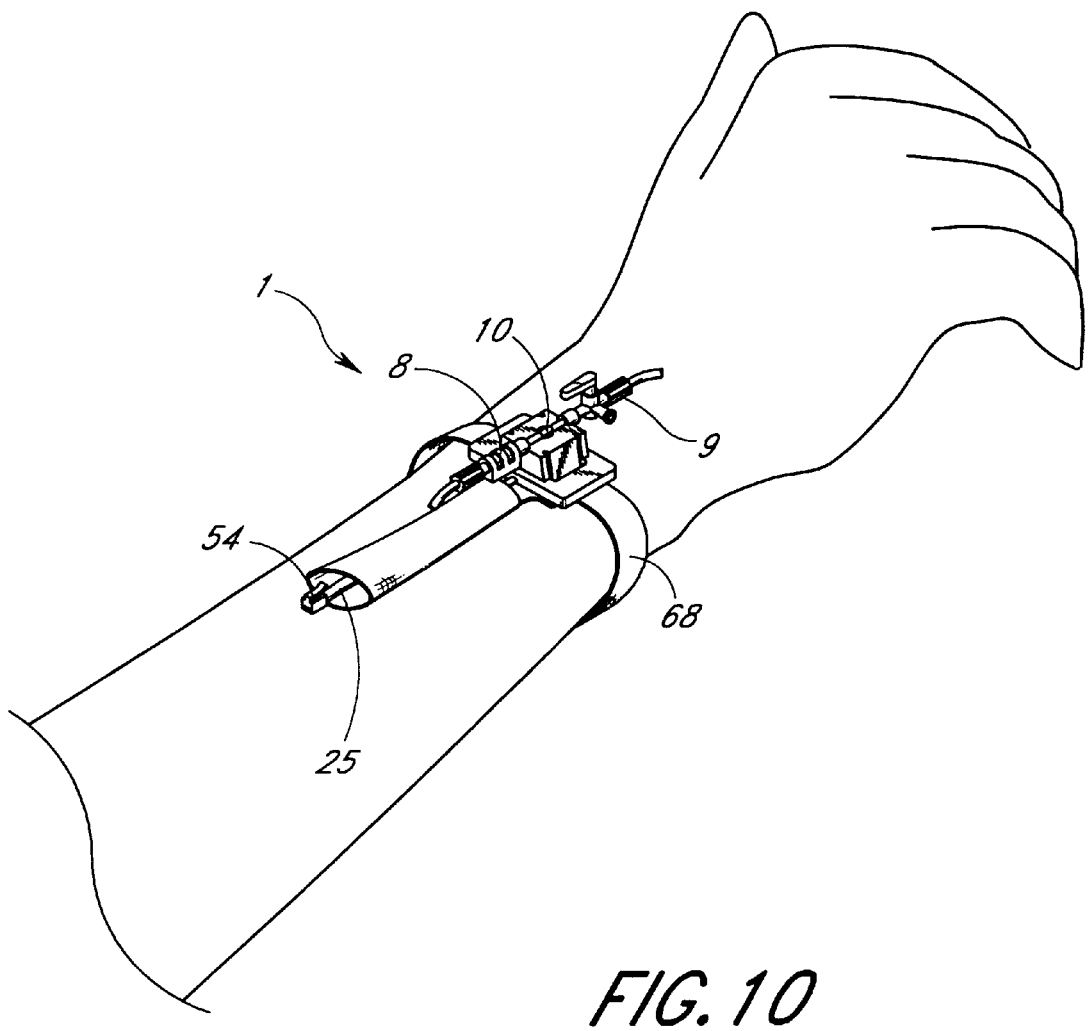
FIG. 10 is a perspective view of a fourth embodiment of the present invention as worn on a user's forearm.

With reference to FIG. 10, there is illustrated a perspective view of a fourth embodiment of the present invention. As shown, the fourth embodiment of the pressure transducer assembly 1 includes an inlet fluid port 8 and an outlet fluid port 9. This embodiment of the pressure transducer assembly 1 is worn by fastening bands such as velcro straps 68 around a patient's forearm. Preferably, the patient wears the pressure transducer 1 in the wrist vicinity, such as in the position in which a wristwatch is normally worn.

Figure 11:
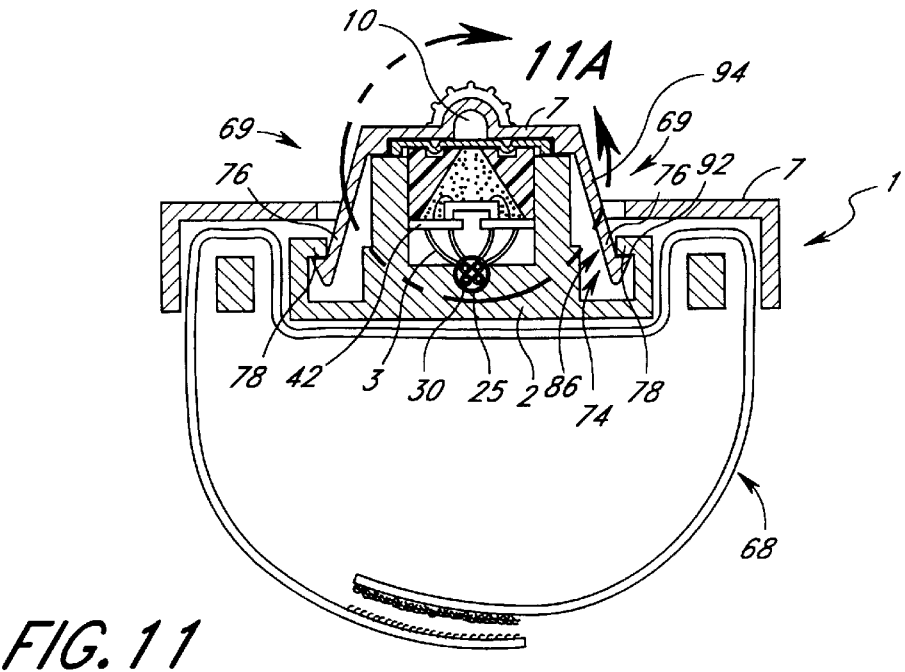
FIG. 11 is a cross-sectional view of the fourth embodiment of the present invention.
Figure 11A:
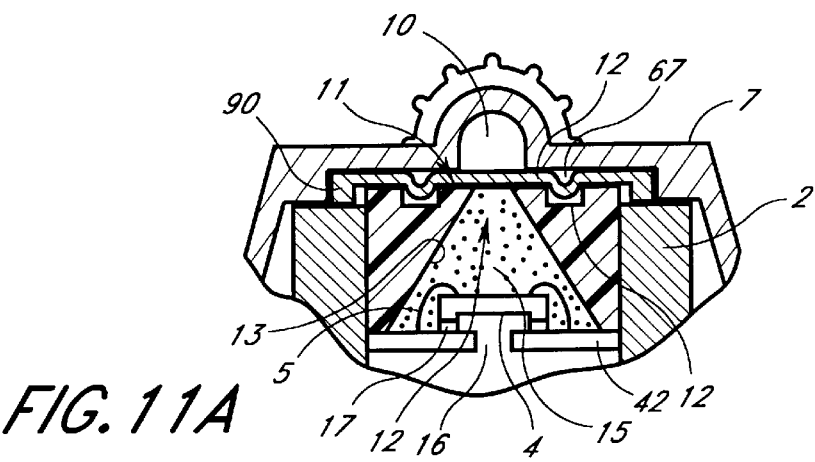
FIG. 11A is a close-up cross-sectional view of the portion of the fourth embodiment of the present invention as defined by the arrow 11A in FIG. 11.
Figure 11B:
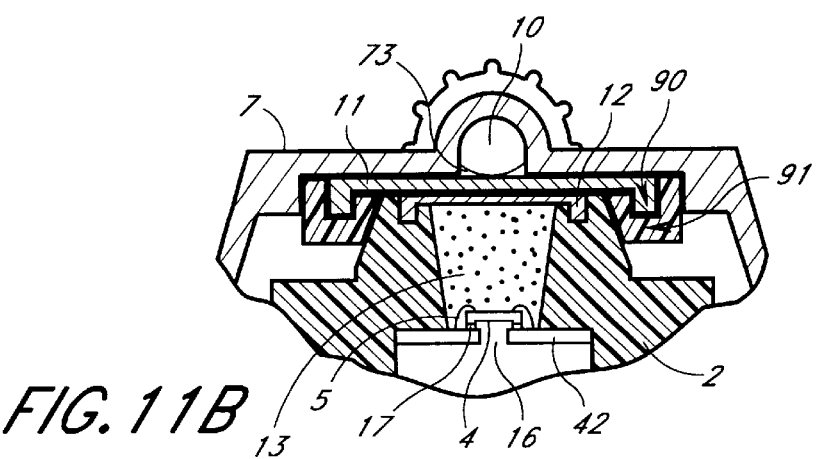
FIG. 11B is a close-up cross-sectional view of a portion of an alternate embodiment.

With reference to FIGS. 11, 11A and 11B, there is illustrated a cross-sectional view of the fourth embodiment of the pressure transducer assembly 1. This particular embodiment utilizes a "snap-fit" mating between the disposable dome 7 and the reusable portion 2 in accordance with the present invention. In addition to the advantages of previous embodiments, this configuration preferably minimizes the amount of sterile plastic materials that must be discarded after each patient application of the pressure transducer assembly 1. Furthermore, this configuration of the fourth embodiment minimizes both patient and staff biocontamination risks.

FIGS. 11 and 11A illustrate the reusable portion 2 and the disposable dome 7 in an assembled state, specifically where the disposable dome 7 is snap-fitted to the reusable portion 2. The disposable dome 7 includes a smooth walled, and preferably substantially straight through fluid filling path and central fluid chamber 10. The fluid chamber 10 communicates with and is preferably defined in part by a surface of the biological isolating medium 11. One side of the isolating medium 11 is in pressure transmitting contact with a diaphragm 12, and sealed against said diaphragm by annular sealing edge 67. Isolating medium 11 may be composed of approximately 10 mil thick 70 Durometer medical grade silicone rubber. Desirably, 70-durometer silicone appears to provide adequate rupture resistance to prevent breaching of the sterile barrier and contamination or escape of the catheter fluid when the dome is removed from the transducer base 2. A silicone O-ring structure 90 is preferably formed on the outer edge of medium 11 to provide a secure mounting means for the diaphragm.

Medium 11 thus forms a part of disposable dome portion 7 and is in pressure transmitting contact with pressure transmitting medium 15, which contains an integral diaphragm 12 at its contacting surface, as previously described.

Alternatively, as shown in FIG. 11B, the medium 11 including O-ring 90 may be secured by a holding and retaining structure 91. To further improve the smoothness of the fluid path to avoid trapping air bubbles, the isolating medium 11 may include a small amount of silicone gel which may be dripped upon and cured on top of a preformed diaphragm which is made from silicon rubber as described above. Preferably, the gel 73 will advantageously form inside of all of the sharp corners around the outer diameter of the preformed diaphragm where it contacts the disposable dome 7, thus providing an extremely smooth and essentially straight through interior fluid path, while providing additional electrical biological isolation of the catheter fluid.

Being responsive to the hydraulic signal as presented by medium 11, a 10 mil thick diaphragm 12 made from nitrile rubber conveys the hydraulic pressure signal into the second chamber 13, and then via pressure transmitting media 15 to the sensor chip 4. In the embodiment of FIG. 11B, the cross sectional area of the chamber 13 adjacent the diaphragm 12 is greater than the cross sectional area of the chamber 13 adjacent the chip 4. The pressure transmitting media 15 may comprise silicone gel. The chip 4 is attached to the floor of the second chamber 13 by a silicon chip carrier 42, such as a thick-film network, and a silicone adhesive sealant 17. Wire bond leads 5 carry the pressure signal from the chip 4 to a cable 25, and ultimately to an electrical interface connector 54 (FIG. 10). The sensor vent tube 30 conveys an atmospheric reference pressure to one side of pressure sensor chip 4 via vent hole 16. Sensor vent tube 30 is vented on its proximal end at connector 54 (See FIG. 12), and at it's distal end it connects to vent hole 16 as it exits the back side of thick film substrate 42.

A particular advantage of this embodiment is that the transducer disposable portion 7 is quickly and easily attached and detached from the reusable portion 2 using snap-on attachment structures 74. The attachment structures 74 preferably consist of one or more and preferably two compressible barbs 76 which are premolded into opposite sides of the disposable dome 7. A set of receiving tabs 78 are formed in the reusable portion 2. The barbs 76 are configured to mate with tabs 78 in order to removably secure the disposable dome 7 to the reusable portion 2. The user grasps and compresses the barbs 76 at locations 69 while pulling upward in order to release the disposable dome 7 from the reusable portion 2. To reattach the dome 7, the user simply pushes the dome 7 onto the reusable portion so that the barbs 76 engage with the tabs 78 and thereby lock the dome 7 in place.

In general, the snap interfit structure between the reusable portion 2 and the disposable dome 7 can be based upon an interference fit, ratchet type structure, friction fit or other depending upon the desired product characteristics. In a typical product, at least one interference surface 92 connected to or on the dome 7 releasably engages at least one corresponding surface attached to or on the reusable portion 2. In the embodiment illustrated in FIG. 11, the interference surface 92 appears on the barb 76 engaged with the complementary surface on tab 78. The interference surface 92 is connected to the dome 7 by way of a flexible arm 94 which preferably biases the interference surface 92 in the direction of the complementary surface on reusable portion 2. Thus, overcoming the bias created by the arm 94 permits the interference surface 92 to extend through an aperture 86 on the reusable portion 2. Releasing the compression force permits the bias in the arm 94 to engage interference surface 92 with the corresponding surface on the reusable portion 2. Although a single two part locking structure having the foregoing characteristics can be used, preferably two opposing locking structures as illustrated in FIG. 11 will be used to securely mount the two components of the pressure transducer together.

Any of a variety of alternate releasable snap-fit type structures can be used as will be apparent to those of skill in the art, as long as the structure selected provides a sufficient compression to produce an adequate propagation of the pressure signal across the interface between medias 11 and 15.

In the embodiment of FIG. 11, the biological isolating medium 11 and the diaphragm 12 are both preferably made from soft elastomeric material with their thickest vertical cross sections located along their outer peripheries. The two protrusions 67 compress the two elastomeric materials as the disposable dome 7 is advanced against the reusable portion 2. The resulting compression between the protrusions 67 and the elastomeric materials preferably provides a spring force to hold the engagement surface 92 on barbs 76 firmly engaged against the complementary surface on tabs 78 of the reusable portion. This snap-type fit thus holds the disposable dome 7 firmly attached to the reusable portion 2 with sufficient spring force to provide excellent hydraulic signal transmission between the two parts. The orientation of the two elastomeric materials with their thicker outermost retaining sections extending away from the fluid path, provides the special benefit of an essentially straight through fluid path through the disposable dome 7 which is unique in the field of disposable domes for a reuseable transducer. Heretofore, disposable domes for reusable transducers have been designed with their isolating mediums (i.e. diaphragms) thickest vertical retaining portion facing upward from the pressure transmitting surface, thus necessitating a crooked or stepped flow path through the dome, which often results in the undesirable entrapment of bubbles. Thus, the novel shape of isolating medium 11 in the various embodiments of the invention as herein described provides special benefits for ease of use comparable to fully disposable transducer designs.

Figure 12:
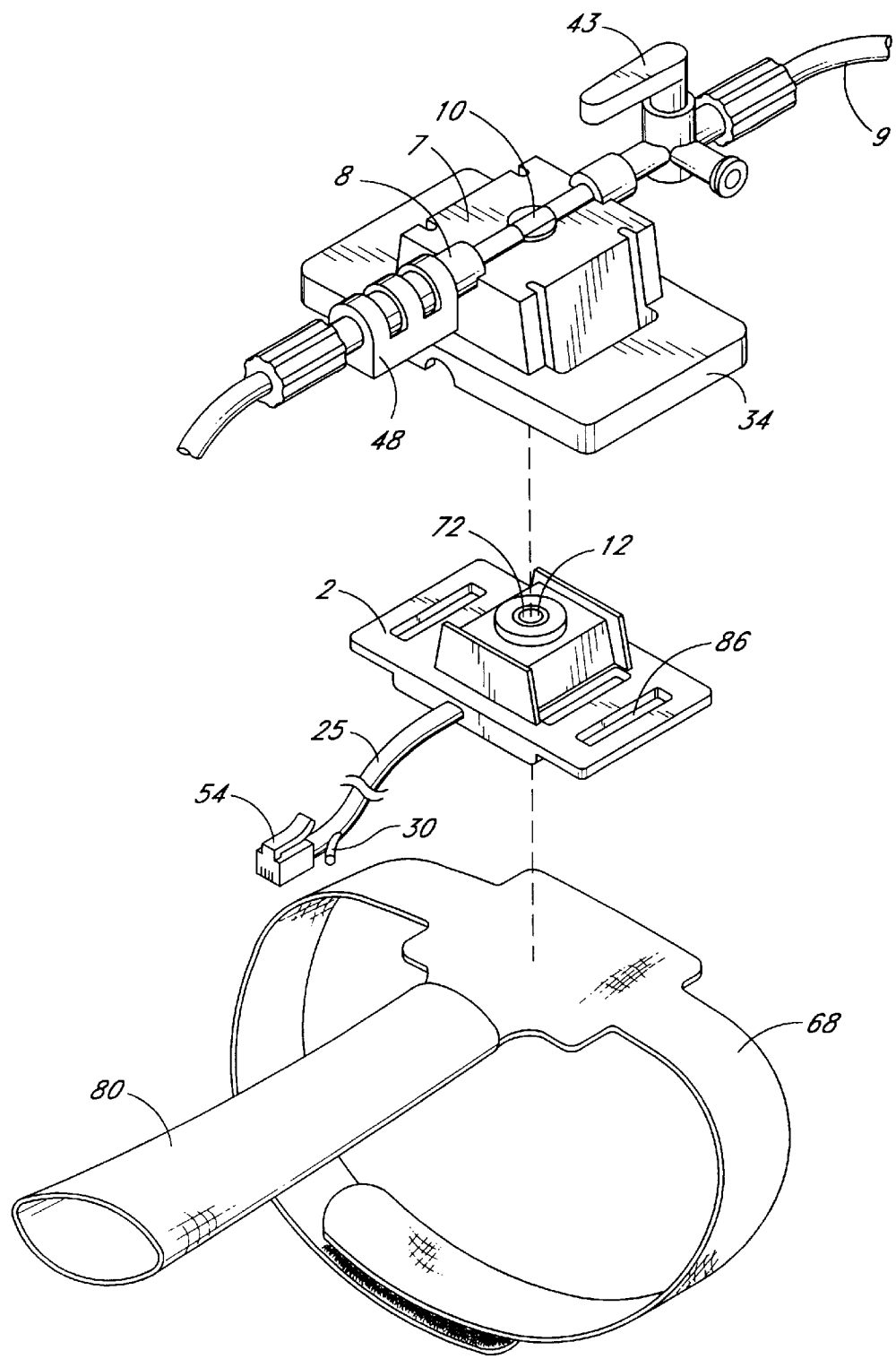
FIG. 12. is an exploded, perspective view of the dome portion and reusable portion of the fourth embodiment of the present invention.

FIG. 12 illustrates a perspective view of the fourth embodiment of the pressure transducer 1, where the reusable portion 2 and disposable dome 7 are disassembled from one another. As shown, a sterile sheath 80 has tubular shape and is preferably made from thin polyethylene or other plastic flexible tubing. The sterile sheath 80 houses the cable 25 and electrical connector 54 during use. Certain portions of the snap-fit pressure transducer structure, including the disposable dome 7, the velcro strap 68, and the sheath 80 are preferably supplied sterile and made to completely shroud the reusable portion 2 of the transducer 1 when assembled. In clinical use, the reusable portion 2 may be cleaned but need not necessarily be sterile. Thus, this embodiment is intended for direct mounting of the transducer assembly 1 to the patient, as may be often be advantageous when transporting the patient, or when the physician desires to reduce the catheter and tubing length to obtain higher fidelity pressure recordings. As illustrated in FIG. 11, the velcro strap 68 is used to securely attach the transducer assembly 1 to the patient's wrist or forearm during such use, by threading the strap ends through the outer slots in the reusable housing 2, and thence around the patient's forearm or other appendage.

Figures 13A, 13B:
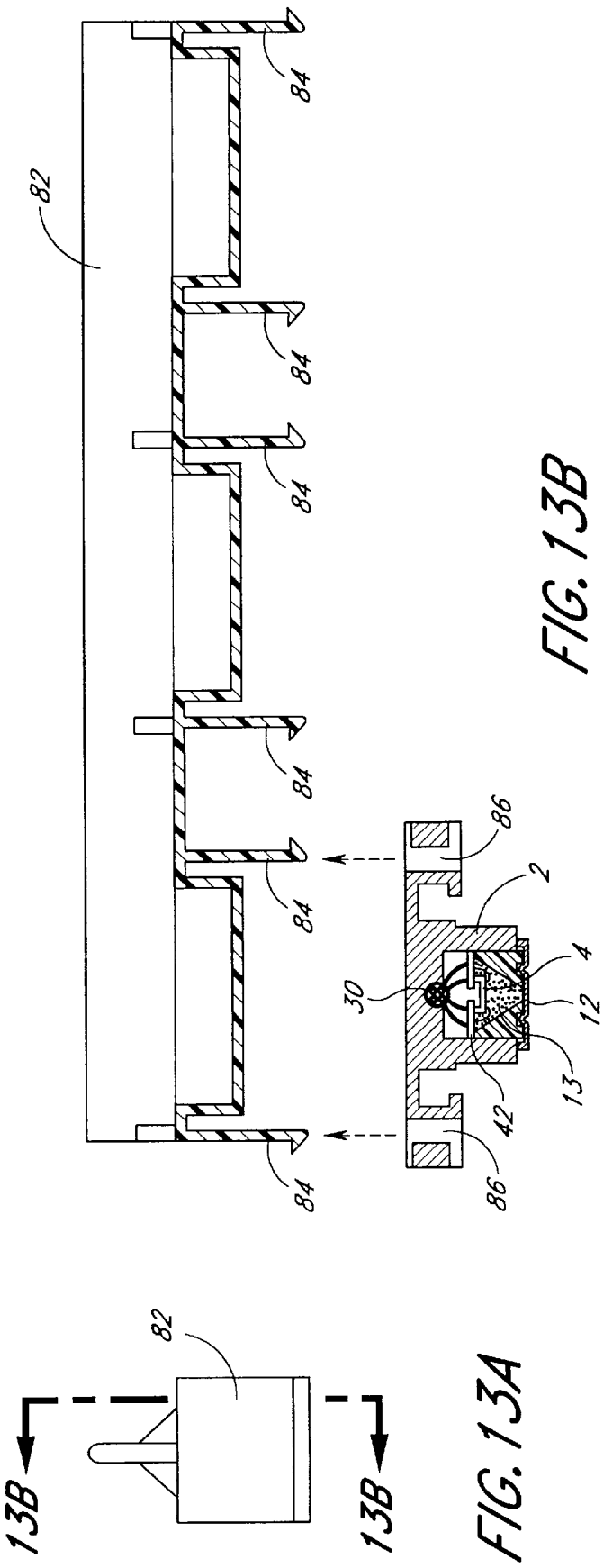
FIG. 13A is a side view of an IV pole mounting adapter assembly which may be used in conjunction with the present invention.
FIG. 13B is a cross-sectional view of the IV pole adapter assembly illustrated in FIG. 13A taken along the line 13B—13B, along with a horizontal cross-sectional view of a mating reusable transducer.

FIGS. 13A and 13B illustrate an adaptor accessory 82 that may be used to mount one or more of the fourth embodiment of the present invention to an IV pole manifold holder assembly. As shown in FIG. 13B, a plurality of accessory barbs 84 extend outward from the adaptor accessory 82. The accessory barbs 84 are preferably arranged in sets of two and are configured to mate with apertures 86 in the reusable portion 2 of the transducer assembly 1. This allows the reusable portion 2 to be removably mounted to an IV pole or other convenient support structure through the adaptor accessory 82 in a snap-fit manner. Hence, the fourth embodiment of the invention may be quickly removed from the patient and mounted to an IV pole manifold holder assembly using the adapter accessory 82 shown in FIGS. 13A and 13B.

This option may be of particular advantage when the patient reaches an intensive care ward, where it is desired to put the transducer in a more fixed location adjacent to the monitoring equipment. To use this accessory, the velcro straps 68 located at the patient's wrist are disconnected and the transducer assembly 1 is removed from the patient's arm. During this procedure, sterile technique is preferably maintained and the transducer preferably continues to monitor the patient blood pressure signals. The velcro strap 68 is then pulled from the back of the transducer assembly 1, and the remaining pieces of the transducer assembly, namely the reusable portion 2, assembled to disposable dome 7, is snapped into a waiting adapter accessory 82, which has been pre-attached to an IV pole manifold holder 50, such as the type as illustrated in FIG. 9.

Thus, the embodiment as shown in FIGS. 10–13 facilitates easy configurability to a variety of clinical situations based on the snap-together feature of the present invention. The present invention also provides economic savings for the hospital since the reusable portion 2 of the transducer assembly 1 may be easily reused by the clinical staff without resort to expensive re-sterilization techniques. The cost of manufacturing the single use sterile materials that are discarded after each application is also considerably lower than the cost of manufacture of a fully disposable, single-use transducer with integral sensor chip.

While the present invention has been disclosed with respect to the preferred embodiments thereof, those of ordinary skill in the art will understand that further modifications to the invention may be made within the scope of the claims that follow hereinbelow. Accordingly, it is not intended that the scope of the invention be limited to what has been disclosed above but, instead, should be determined entirely by reference to the claims that follow.

What is claimed is:

1. A disposable dome for use in combination with a reusable sensor to form a reusable transducer assembly for measuring pressure in a fluid line coupled to a catheter inserted into a living body for making direct pressure measurements in areas within the body of medical interest, said disposable dome including a fastener arranged to releasably engage a complementary surface on the reusable sensor and discardable after a single use, said dome including an electrically and biologically isolating coupling media shaped in conjunction with the dome to form a straight through fluid filling path, and wherein said media transmits hydraulic pressure signals from a fluid-filled chamber in said dome to the reusable sensor.

2. The apparatus according to claim 1 wherein the coupling media comprises one or more elastomers in an interior cavity of the disposable dome, the elastomer forming a smooth internal path for the flow of fluid.

3. The apparatus according to claim 2 wherein the elastomer is at least in part a silicone gel.

4. The apparatus according to claim 2 wherein the elastomer is cast, cured, or formed in place within the disposable dome to form a convex pressure transmitting surface prior to assembly onto the reusable sensor.

5. The apparatus of claim 1 wherein said isolating medium is U-shaped, with the legs of the 'U' pointing away from the fluid path and in the direction of the reusable sensor of the transducer.

6. The apparatus of claim 1 wherein said fastener consists of a snap together retaining mechanism which can be disengaged by pressing on the sides of the dome.

7. The apparatus according to claim 1, said assembly comprising;

a housing;

an inlet and an outlet port in the housing, having a fluid flow path extending therebetween;

a cavity in the flow path, said cavity divided into a first and a second chambers by a flexible diaphragm;

said flow path in communication with said catheter and said first chamber within said housing;

said first chamber further containing said isolating media;

said second chamber containing a compensated pressure sensor spaced from said diaphragm with one side of said pressure sensor sealingly disposed in communication with a vent hole in a surface of said chamber, said vent hole providing an ambient air pressure reference to a first side of the pressure sensor;

pressure transmissive media in said second chamber for transmitting hydraulic pressure signals from said diaphragm to a second side of the pressure sensor; and an electrical conductor connected to the pressure sensor and extending from said housing.

8. The apparatus of claim 7, wherein the housing comprises first and second removably securable components with a first component containing the first chamber and said inlet and outlet ports adapted to be removable and disposable after a single use.

9. The apparatus of claim 7, wherein the outlet port is in fluid communication with an integral stopcock having an auxiliary port for zeroing and/or catheter fluid volume manipulation.

10. The apparatus of claim 7, wherein the flexible diaphragm comprises a membrane selected from the group consisting of polyisoprene, mylar, polyamide, stainless steel alloy, high density polyethylene, silicone rubber, and nitrile or butyl rubber.

11. The apparatus of claim 7, wherein the isolating media and the pressure transmissive media comprise dissimilar materials at their contacting surfaces, such that the isolating media and the pressure transmissive when placed in intimate sealing contact do not adhere to one another.

12. The apparatus of claim 7, wherein the diaphragm comprises a surface of the pressure transmissive media in the second chamber.

13. The apparatus of claim 12 wherein said diaphragm is formed by curing a first type of silicone elastomer, and then curing a second elastomer in contact with the first.

14. A disposable dome for use in combination with a reusable sensor to form a reusable transducer assembly for measuring pressure in a fluid line coupled to a catheter inserted into a living body for making direct pressure measurements in areas within the body of medical interest, said disposable dome portion including a fastener arranged to releasably engage a complementary surface on the reusable sensor and discardable after a single use, said dome including an electrically and biologically isolating coupling media shaped in conjunction with the dome, said assembly comprising a housing, an intlet and an outlet port in the housing, having a fluid flow path extending therebetween, and a cavity in the flow path, said cavity being divided into a first chamber and a second chamber by a flexible diaphragm, wherein said coupling media is disposed adjacent to said diaphragm to transmit hydraulic pressure signals from said first chamber to said second chamber via said diaphragm, said coupling media not comprising a diaphragm, and comprising one or more elastomers which form a smooth internal path for the flow of fluid.

15. The apparatus according to claim 14, wherein said coupling media comprises a gel.

* * * * *